US00PP27340P3

(12) United States Plant Patent
Suphachadiwong

(10) Patent No.: US PP27,340 P3
(45) Date of Patent: Nov. 1, 2016

(54) ***DENDROBIUM* ORCHID PLANT 'SPCDW1004'**

(50) Latin Name: ***Dendrobium* hybrid**
Varietal Denomination: SPCDW1004

(71) Applicant: Thumrong Suphachadiwong, Chonburi (TH)

(72) Inventor: Thumrong Suphachadiwong, Chonburi (TH)

(73) Assignee: Suphachatwong Innovations Ltd (TH)

( * ) Notice: Subject to any disclaimer, the term of this patent is extended or adjusted under 35 U.S.C. 154(b) by 281 days.

(21) Appl. No.: 13/999,299

(22) Filed: Feb. 6, 2014

(65) Prior Publication Data

US 2014/0223627 P1 Aug. 7, 2014

(30) Foreign Application Priority Data

Feb. 7, 2013 (QZ) ..... PBR A201300293

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — June Hwu
(74) *Attorney, Agent, or Firm* — Cassandra Bright

(57) ABSTRACT

A new and distinct *Dendrobium* cultivar named 'SPCDW1004' is disclosed, characterized by its large pure white flower. The new variety is a *Dendrobium*, typically produced as an indoor ornamental plant.

1 Drawing Sheet

Latin name of the genus and species: *Dendrobium* hybrid. Variety denomination: 'SPCDW1004'.

BACKGROUND OF THE INVENTION

This application relates to a new cultivar of *Dendrobium* hybrid. The new variety is the product of a planned breeding program. The new variety originated as a seedling from the crossing of the unpatented, proprietary seed parent *Dendrobium* 'SK151' with the unpatented, proprietary pollen parent referred to as *Dendrobium* 'PTW'. The crossing was made by the inventor in his research greenhouse in Chonburi, Thailand in October of 2000.

The new variety was first selected by the inventor, Thumrong Suphachadiwong, a citizen of Thailand, in March of 2006 in a research greenhouse belonging to the inventor in Chonburi, Thailand. After identifying the new variety as a potentially interesting selection, the inventor continued confidential testing and propagation of 'SPCDW1004', assessing stability of the unique characteristics of this variety.

Asexual reproduction of the new cultivar 'SPCDW1004' was first performed at a commercial laboratory belonging to the inventor in Chonburi, Thailand by tissue culture, using meristem culture in March of 2006. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SPCDW1004' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPCDW1004.' These characteristics in combination distinguish 'SPCDW1004' as a new and distinct *Dendrobium* cultivar:

1. Pure white flowers.
2. Large flower size.

PARENT COMPARISON

Plants of the new cultivar 'SPCDW1004' are similar to the seed parent, *Dendrobium* 'SK151' in most horticultural characteristics. However the new variety, 'SPCDW1004' differs from 'SK151' in the following characteristics:

1. Parent has light pink flowers 'SPCDW1004' has pure white flower.

Plants of the new cultivar 'SPCDW1004' are similar to the pollen parent, *Dendrobium* 'PTW' in most horticultural characteristics. However the new variety, 'SPCDW1004' differs from 'PTW' in the following characteristics:

1. Spikes produce more flowers and grow more upright.
2. More compact plant.
3. Smaller flower size.

COMMERCIAL COMPARISON

'SPCDW1004' is similar in most horticultural characteristics to the unpatented commercial variety *Dendrobium* 'White Surprise' in most horticultural characteristics. However the new variety, 'SPCDW1004' differs from 'White Surprise' in the following characteristics:

1. Smaller flower size.
2. Shorter plant height.
3. Narrower sepals.
4. Different column color.

Plants of the new cultivar 'SPCDW1004' are also comparable to the unpatented commercial variety *Dendrobium* 'Snow Jade'. The two *Dendrobium* varieties are similar in most horticultural characteristics; however, the new variety 'SPCDW1004' differs in the following ways:

1. Different lip shape.
2. Narrower dorsal and lateral sepal shape.
3. Pure white flower. The comparator flowers are greenish white.

BRIEF DESCRIPTION OF THE PHOTOGRAPH

The accompanying photograph in FIG. 1 illustrates in full color a typical plant of 'SPCDW1004' grown in a commercial greenhouse in Honselersdijk, the Netherlands. The plant is 1 years old from a rooted cutting, in a 10.5 cm pot.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SPCDW1004' plants grown in a commercial greenhouse in Honselersdijk, the Netherlands. The plant is 1 year old from a rooted cutting, in a 10.5 cm pot. Temperatures ranged between 26° C. and 30° C. day and night. No photoperiodic or chemical treatments were given to the plants. The light sum was set at 5 moles per day and the plant was given shading and artificial light in order to come to the light sum of 5 moles per day. Both shading and artificial lightning were frequently applied in order to achieve the ideal light sum of 5 moles per day. Measurements and numerical values represent averages of typical plant types.

Botanical classification: *Dendrobium* hybrid 'SPCDW1004'.

PROPAGATION

Type of propagation typically used: Tissue culture, using meristem culture. The very growing center of a new growth bud is taken and grown on by agitating constantly in a special nutrient rich liquid until the cell mass is large enough to be split in to small sections these are then either grown on in to plants or the process is repeated to produce more tissue for growing on. This method is often used to mass produce a specific hybrid for commercial purposes.

Time to initiate roots: Tissue culture takes 18 months. After deflasking it takes another 9 to 12 months to get a well-rooted plant under average temperatures ranging between 26 en 30 degrees Celsius. After planting in the end pot, the young plant already has roots and those roots continue to grow in the end pot almost right away and certainly within 8 days.

Time to produce a rooted cutting/liner: Tissue culture takes 18 months. After deflasking it takes another 9 to 12 months to get a well-rooted plant under average temperatures ranging between 26 en 30 degrees Celsius. After planting in the end pot, the young plant already has roots and those roots continue to grow in the end pot almost right away and certainly within 8 days.

Root description:

*Root color*.—Yellow-white near RHS 158D.
*Average diameter*.—Average: 0.2 cm.
*Average length*.—Lateral roots average: 4.8 cm.

PLANT

Growth habit: Sympodial, upright.
Height from top of soil line to top of foliage: 31.0 cm.
Height from top of soil line to top of flowers: 48.5 cm.
Plant spread: 21.5 cm.
Normal pot size: 10.5 cm circular pot.
Growth rate: Moderate.
Number of leaves per plant: Average: 12.
Plant stem:

*Length*.—Approximately 13.2 cm.
*Diameter*.—Approximately 1.7 cm.
*Aspect*.—Approximately 75° angle to soil surface (=0°).
*Strength*.—Strong.
*Texture*.—Glabrous, very slightly glossy, axially ribbed.
*Color*.—Yellow-green, in between near RHS N144A and 152C.
*Pseudobulb*.—Longitudal section shape: Lanceolate. Cross section shape: Circular.

FOLIAGE

Leaf:

*Arrangement*.—Distichous.
*Average length*.—Approximately 12.5 cm.
*Average width*.—Approximately 4.3 cm.
*Shape of blade*.—Narrow Ovate to elliptic.
*Aspect*.—Leaves in an average angle of 70° to main stem (=0°).
*Apex*.—Acute.
*Base*.—Sheathing. Sheath length: Average 3.0 cm. Sheath width: Average 1.6 cm. Sheath color: Yellow-green, near RHS 147D, slightly striped axially, yellow-green; near RHS 147B, stripes coloured purple near the base; near RHS N79A.
*Margin*.—Entire.
*Texture of top surface*.—Glabrous, moderately glossy.
*Texture of bottom surface*.—Glabrous, matte.
*Durability to physical stress*.—High.
*Color*.—Young foliage upper side: Green; in between near RHS 137A and 143A. Young foliage under side: Yellow-green; near RHS 147B. Mature foliage upper side: Green; in between near RHS N137A and 143A but darker. Mature foliage under side: Yellow-green; near RHS 146A to 146B.
*Venation*.—Type: Parallel. Venation coloration: Upper Surface: Green; in between near RHS N137A and 143A but darker. Lower Surface: Yellow-green; near RHS 146B.

Petiole: No petioles present.

FLOWERING CHARACTERISTICS

Flower bud:

*Rate of opening*.—Approximately 30 days from first sight.
*Length*.—Approximately 2.4 cm.
*Diameter*.—Approximately 1.1 cm.

*Shape*.—Ovate; curved.
*Color*.—Yellow-green; near 145B, tip of spur purple; near RHS N77B.

Peduncle:
*Length*.—Approximately 26.0 cm.
*Diameter*.—Approximately 0.3 cm.
*Aspect*.—Approximately 0° angle to stem.
*Strength*.—Strong.
*Texture*.—Glabrous, slightly glossy.
*Color*.—Yellow-green; near RHS 144A, sunny side tinged darker; near RHS 146A.

Inflorescence:
*Flowers per stem*.—Average: 10.
*Inflorescence arrangement*.—Simple raceme, flowers positioned along peduncle.
*Inflorescence height*.—Approximately 17.5 cm (from lowest pedicel to top of inflorescence).
*Inflorescence width*.—Approximately 10.8 cm.

Individual flowers:
*Flower type*.—Single, orchidaceous (zygomorphic), typical for *Dendrobium*.
*Rate of opening*.—After the first flower has opened, it takes approximately four weeks before the top flower opens.
*Shape*.—Orchidaceous (zygomorphic), typical for *Dendrobium*, with three sepals, two lateral petals and a labellum (third petal).
*Height*.—Approximately 5.7 cm.
*Diameter*.—Approximately 6.4 cm.
*Depth*.—Approximately 3.4 cm.
*Fragrance*.—No fragrance.
*Lastingness*.—Individual flowers can last up to 9 weeks on the plant.
*Persistent*?.—Non-persistent.
*Quantity of petals*.—Average: 3 (two lateral petals and a labellum (=third petal)). Only the two lateral petals are described here as such.

Petals:
*Arrangement*.—Oppositely placed on each side of the column.
*Length*.—Approximately 3.5 cm.
*Width*.—Approximately 3.2 cm.
*Shape*.—Broad obovate, slightly curved.
*Apex*.—Rounded.
*Base*.—Cuneate.
*Margin*.—Entire.
*Appearance*.—Both sides matte, velvety.
*Texture, upper forward surface*.—Glabrous, velvety.
*Texture, lower back surface*.—Glabrous, velvety.
*Color*.—When opening, forward surface: White; near RHS NN155D, base red-purple; near RHS 72B. When opening, back surface: White; near RHS NN155D, base slightly darker; near RHS NN155A, base at point of petal attachment red-purple; near RHS 72B. Fully Opened, forward surface: White; near RHS NN155D, base red-purple; near RHS 72B to 72C. Fully Opened, back surface: White; near RHS NN155D, base slightly darker; near RHS NN155A, base at point of petal attachment red-purple; near RHS 72B to 72C. Fading, forward surface: not fading (colours similar to "Fully Opened"). Fading, back surface: not fading (colours similar to "Fully Opened"). Color Venation Fully Opened, forward surface: White; near RHS N155D, veins at The base colored red-purple; near RHS 72B and 72C. Color Venation Fully Opened, back surface: White; near RHS N155D, veins at the base slightly darker, near RHSN155A, colored red-purple at adjacent petal attachment (base); near RHS 72B and 72C.

Labellum:
*Shape*.—Deltoid, three-lobed, strongly involute.
*Length*.—Approximately 2.8 cm.
*Width*.—Approximately 2.1 cm (when "folded open", approximately 3.4 cm).

Lateral lobe:
*Shape*.—Obovate.
*Length*.—Average: 2.0 cm.
*Width*.—Average: 1.2 cm.
*Tip*.—Abruptly acute.
*Base*.—Broad cuneate.
*Texture*.—Glabrous, velvety.
*Appearance*.—Matte moderately velvety.
*Margin*.—Entire.
*Color*.—When opening, forward surface: Near RHS White N155C, base near Yellow-Green 150D. When opening, back surface: Near RHS White N155C, base near Yellow-Green 150D. Fully Opened, forward surface: Near RHS White N155C, base near Yellow-Green 150D. Fully Opened, back surface: Near RHS NN155C, base near Yellow-Green 150D.

Apical lobe:
*Shape*.—Narrow obovate.
*Length*.—Average: 2.8 cm.
*Width*.—Average: 2.1 cm.
*Tip*.—Abruptly acute.
*Base*.—Broad cuneate.
*Texture*.—Glabrous, velvety.
*Appearance*.—Matte moderately velvety.
*Margin*.—Entire.
*Color*.—When opening, forward surface: Near RHS White N155C. Slightly flushed purple; 77C and 77D, base near Yellow-Green 150D. When opening, back surface: Near White RHS N155C. Fully Opened, forward surface: Near RHS White N155C, slightly flushed purple; 77C and 77D. Base near Yellow-Green 150D. Fully Opened, back surface: Near RHS White N155C.
*Callosites*.—Dimensions: Average: 1.8 cm long and 0.5 cm wide. Location: central placed on the labellum, coloured yellow-green; near RHS 150D and lighter.
*Lip eye*.—Absent.
*Lip twisting*.—Absent.
*Lip undulation*.—Absent.
*Lip fringing of the margin*.—Absent.
*Lip pubescence*.—Absent.

Sepals:
*Quantity*.—Average: 3.
*Appearance*.—Matte, velvety.
*Length*.—Approximately 3.5 cm.
*Width*.—Dorsal sepal, approximately 1.6 cm. Lateral sepals, approximately 1.9 cm.
*Shape*.—Dorsal sepal elliptic to oblong. Lateral sepals ovate, falcate.
*Apex*.—Acute.
*Base*.—Broad cuneate.
*Margin*.—Entire, without twisting or undulation.
*Texture*.—Glabrous, velvety.

*Color*.—Forward surface: White; near RHS NN155D. Back surface: White; near RHS NN155D.

*Mentum*.—Average width: 0.3 cm. Average length: 0.8 cm. Color: Near RHS Yellow-Green 146D.

Pedicels:

*Length*.—Approximately 3.2 cm.

*Diameter*.—Approximately 0.2 cm.

*Angle*.—Approximately 60° angle to peduncle (=0°).

*Strength*.—Moderately strong.

*Texture*.—Glabrous, moderately glossy.

*Color*.—Green-white; near RHS 157A, base yellow-green; near RHS 144C.

REPRODUCTIVE ORGANS

Stamens, style and stigma fused into column?: Yes.

Column length: Average: 0.6 cm.

Column diameter: Average: 0.8 mm.

Column color: Green-white; near RHS 157D.

Anther cap:

*Average width*.—0.35 cm.

*Average length*.—0.25 cm.

*Color*.—Near RHS White N155B.

Ovary:

*Position*.—Superior, placed directly above stigma.

*Diameter*.—Average: 0.2 cm.

*Color*.—Green-white; near RHS 157A.

Stigma:

*Shape*.—Clavate.

*Color*.—Green-white; near RHS 157A.

*Dimensions*.—Average: 0.3 cm high and 0.3 cm wide.

Pollinia:

*Color*.—Yellow-orange; near RHS 14A.

*Dimensions*.—Average: 0.075 cm long and 0.1 cm wide.

*Quantity*.—2.

OTHER CHARACTERISTICS

Disease and pest resistance: High tolerance for typical diseases and pests of *Dendrobium*.

Drought tolerance and cold tolerance: Normal for Genus.

Fruit/seed production: No fruits/seeds detected to date.

What is claimed is:

1. A new and distinct cultivar of *Dendrobium* plant named 'SPCDW1004' as herein illustrated and described.

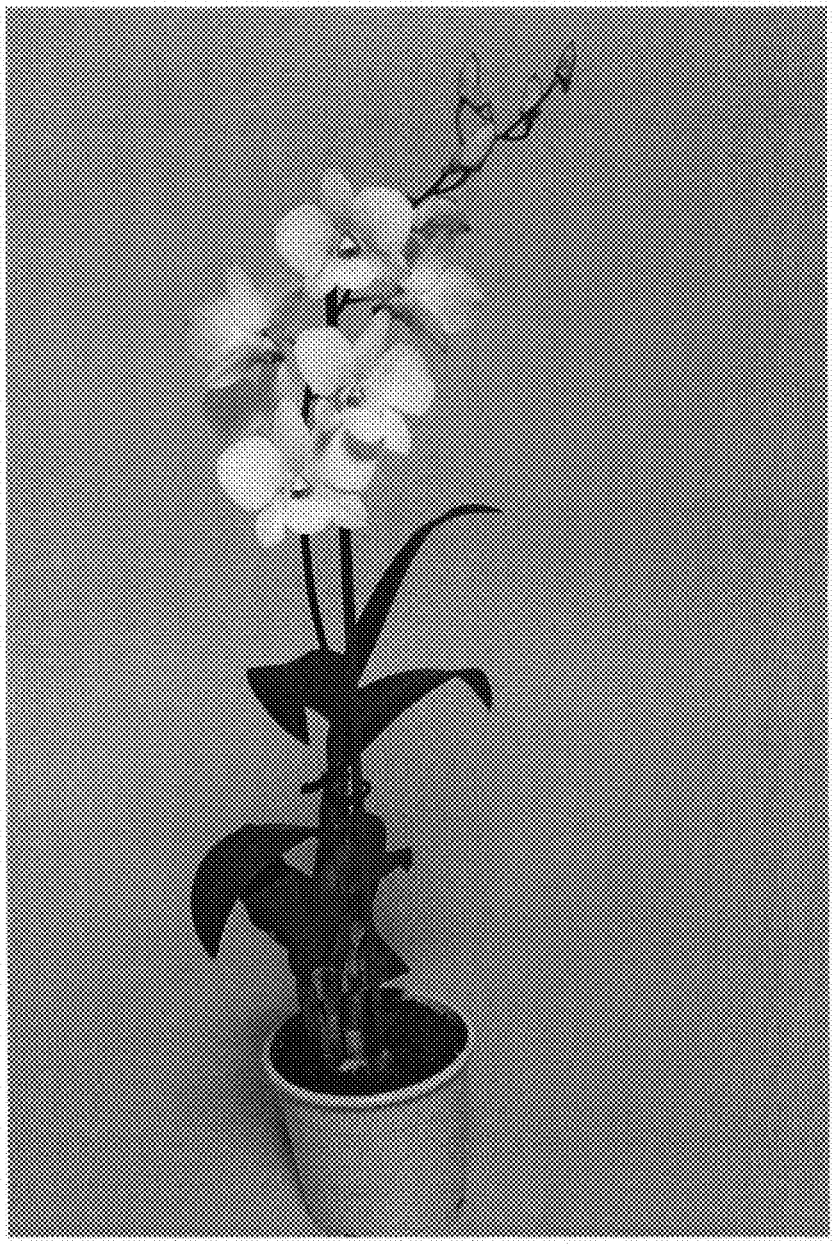

* * * * *